United States Patent
Gordon et al.

(10) Patent No.: US 7,265,676 B2
(45) Date of Patent: Sep. 4, 2007

(54) ALERT SYSTEM AND METHOD FOR AN IMPLANTABLE MEDICAL DEVICE

(75) Inventors: Paul G. Gordon, St. Louis Park, MN (US); Javaid Masoud, Shoreview, MN (US); James J. Ball, St. Paul, MN (US); Holly S. Vitense, Maple Grove, MN (US); James E. Willenbring, St. Paul, MN (US); John P. Vandanacker, Greenfield, MN (US); Sean B. McAdams, Minneapolis, MN (US); Dean A. Hooper, Oak Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 157 days.

(21) Appl. No.: 10/977,242

(22) Filed: Oct. 29, 2004

(65) Prior Publication Data

US 2006/0017576 A1  Jan. 26, 2006

Related U.S. Application Data

(60) Provisional application No. 60/589,250, filed on Jul. 20, 2004.

(51) Int. Cl.
*G08B 23/00* (2006.01)

(52) U.S. Cl. .............................. 340/573.1; 340/539.1; 340/539.12; 600/300; 600/301; 600/306; 705/2; 705/3; 705/424; 705/427; 707/9; 707/10

(58) Field of Classification Search ............. 340/573.1, 340/539.1, 539.12; 600/300, 301, 306, 424, 600/427; 705/2–3; 707/9–10
See application file for complete search history.

(56) References Cited

U.S. PATENT DOCUMENTS

| | | | |
|---|---|---|---|
| 5,113,869 A | 5/1992 | Nappholz et al. | |
| 5,404,877 A | 4/1995 | Nolan et al. | |
| 5,720,771 A | 2/1998 | Snell | |
| 6,272,379 B1 | 8/2001 | Fischell et al. | |
| 6,533,733 B1 * | 3/2003 | Ericson et al. | ............... 600/561 |
| 6,681,003 B2 * | 1/2004 | Linder et al. | .......... 379/106.02 |
| 6,701,184 B2 * | 3/2004 | Henkin | ........................ 600/523 |
| 6,980,112 B2 * | 12/2005 | Nee | ......................... 340/573.1 |
| 7,076,299 B2 * | 7/2006 | Thong | ........................... 607/14 |
| 2003/0210147 A1 * | 11/2003 | Humbard | .................. 340/573.1 |

* cited by examiner

*Primary Examiner*—Jeffery Hofsass
*Assistant Examiner*—Samuel Walk
(74) *Attorney, Agent, or Firm*—Paul H. McDowall; Daniel G. Chapik; Girma Wolde-Michael

(57) ABSTRACT

An alert system for alerting a clinician to an occurrence of an event detected by an implantable medical device includes a monitor and a patient management network. The implantable medical device includes a means for detecting the occurrence of the event and initiating a wireless transmission of data related to the event. The monitor is configured to receive the wireless transmission of data and transfer the data. The patient management network is configured to receive the data and store the data on a data storage device. The patient management network includes a web presentation service for creating a website from the data stored on the data storage device, the website configured to alert the clinician to the occurrence of the event.

14 Claims, 10 Drawing Sheets

Patient Alert Setup

○ Clinical Management Alerts　○ Lead/Device Integrity Alerts

| Alert Conditions | Device Tone<br>Enable Urgency | Patient Home Monitor<br>Yes |
|---|---|---|
| OptiVol Fluid Settings... | Off | Off |
| AT/AF Burden and Rate Settings... | All Off | All Off |
| Number of Shocks Delivered in an Episode... | Off | Off |
| All Therapies in a Zone Exhausted for an Episode | Off | Off |

Alert Time... 08:00

[Demonstrate Tones...]　[Undo Pending]　[OK]

FIG. 7

| Patient Alert Setup | | |
|---|---|---|
| ○ Clinical Management Alerts | ◉ Lead/Device Integrity Alerts | |
| Alert Conditions | Device Tone<br>Enable - Urgency | Patient Home Monitor<br>Yes |
| Lead Impedance Out of Range... | 5 of 5 On - High | 5 of 5 On |
| Low Battery Voltage ERI... | On-High | On |
| Excessive Charge Time EOL | On-High | On |
| VF detection OFF 3+ VF or 3+ FVT Rx Off | On-High | On |
| Alert Time... 08:00 | | |
| Demonstrate Tones... | Undo Pending | OK |

Fig. 9

ALERT SYSTEM AND METHOD FOR AN IMPLANTABLE MEDICAL DEVICE

CROSS-REFERENCE TO RELATED APPLICATION(S)

This application claims the benefit of U.S. Provisional Application No. 60/589,250 filed Jul. 20, 2004 for "Alert System And Method For An Implantable Medical Device" by J. Willenbring, J. VanDanacker, P. Krause, J. Masoud, J. Ball, H. Vitense, S. McAdams, and D. Hooper.

INCORPORATION BY REFERENCE

U.S. Provisional Application No. 60/589,250 filed Jul. 20, 2004 for "Alert System And Method For An Implantable Medical Device" by J. Willenbring, J. VanDanacker, P. Krause, J. Masoud, J. Ball, H. Vitense, S. McAdams, and D. Hooper is hereby incorporated by reference in its entirety.

BACKGROUND OF THE INVENTION

The present invention relates to implantable medical devices, and more particularly to an alert system for an implantable medical device.

During the latter portion of the twentieth century, it became common to implant medical devices to provide therapy for a vast number of medical conditions. Such devices included electrical stimulation devices, pain control devices, and drug delivery systems. Additionally and as these devices became more complex, it became necessary to monitor both their operation and the patient's condition.

At the same time, patients with implantable medical devices (IMDs) have come to expect a fuller life post-implant. These expectations often include few, if any, restrictions on their lifestyle. Thus, patients expect a great degree of mobility while their medical condition is being monitored and/or treated by the IMD and their physician. Semi-annual or annual in-office checkups for the IMD and the patient limits the frequency of monitoring. Moreover, the patient feels that he or she must remain close to the clinician's clinic or the hospital where checkups take place. Further, emergency situations may sometimes occur which, in the mind of the elderly patient, demand a very close proximity to the attending clinician. Going to the clinic for frequent check-ups may impose a considerable burden on the patient as well as an overall increase in the cost of healthcare. Accordingly, some IMDs are equipped with a communication system that connects to an interface in such a manner that it is transparent to the patient and yet provides the medical data required by the clinician.

Until recently, data transmission systems within IMDs were only capable of transferring data over a very small distance. Recent advances in wireless telemetry systems, often utilizing radio frequency (RF) systems, have opened the door to a whole host of new technologies. These technologies are reducing the burden on patients to perform routine tasks and are allowing patients to live with greater freedom and fewer restrictions on their lifestyle. However, there still exist multiple ways in which wireless telemetry systems can be utilized to further enhance the freedom of patients and the quality of care that they receive.

For example, some current IMDs require patient interaction when various events occur. An alarm system which creates an audible alarm to alert the patient to the occurrence of an event. The patient then must either initiate a transfer of data to the clinician over the telephone or like systems or must immediately contact a clinician who can assess the situation. A patient who is relying on the therapy of an IMD can become very distressed when an audible alarm in the IMD begins to sound. Conversely, an audible alarm is often not heard by the patient.

BRIEF SUMMARY OF THE INVENTION

The present invention is an alert system and method for alerting a clinician to the occurrence of a physiological or medical event. The alert system includes an IMD implanted within a patient, a monitor, a patient management network, and patient management web clients. The IMD monitors itself and the patient for the occurrence of an event which satisfies clinician-selected alert criteria. When the event is detected, the IMD provides an alert signal based upon the clinician-selected alert settings. The clinician-selected alert settings inform the IMD who should be alerted upon the occurrence of the event, and the type of alert that should be provided. If the clinician-selected alert settings instruct the IMD to inform the clinician of the event (a silent alert), the IMD wirelessly transmits an alert signal to a monitor. The monitor then performs an interrogation of the IMD and receives data from the IMD. The monitor then transfers the data to the patient management network, which processes the data and informs the clinician of the occurrence of the event. The patient management network is also able to communicate with patient management web clients. Patient management web clients allow the patient or the clinician to access a web page that provides further information about the occurrence of the event.

The alert system of the present invention provides a method of retrying the transmission of data from the IMD to the monitor if the initial attempt is unsuccessful. If the transmission is repeatedly unsuccessful, the alert system provides a backup alert, such as an audible alarm, that will inform the patient of the occurrence of the event. In this way, the patient can contact the clinician to inform him or her of the occurrence of the event.

The alert system of the present invention also provides a user interface in which the clinician can set the clinician-selectable alert settings.

BRIEF DESCRIPTION OF THE DRAWINGS

FIGS. 7 and 8 are exemplary screen shots of a user interface allowing the clinician to select clinical management alert settings.

FIGS. 9 and 10 are exemplary screen shots of a user interface allowing the clinician to select lead/device integrity alert settings.

DETAILED DESCRIPTION

Figure 1:
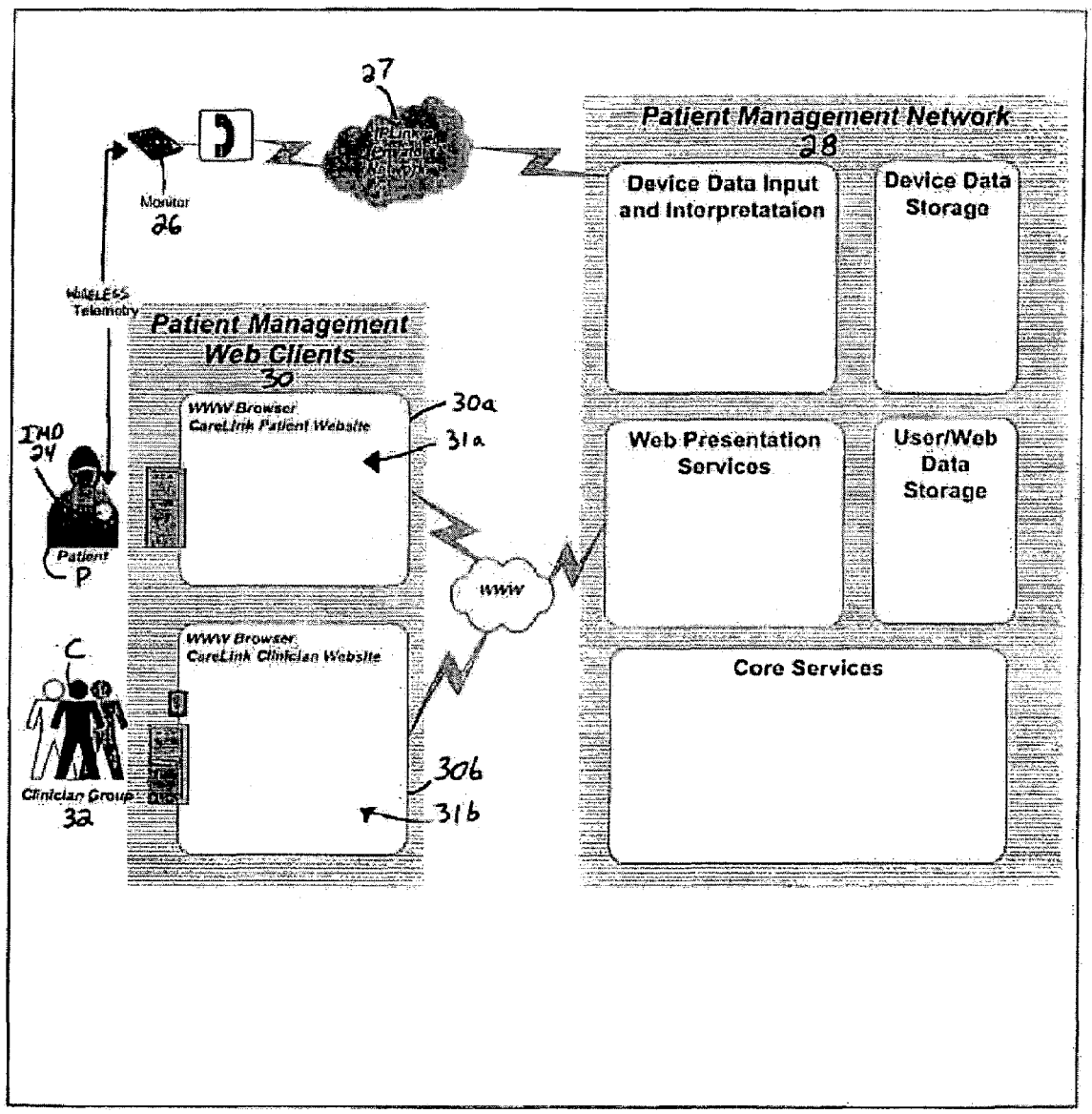
FIG. 1 illustrates a preferred embodiment of the alert system of the present invention.

FIG. 1 illustrates an exemplary embodiment of alert system 20 of the present invention, which communicates between patient P and clinician C. Alert system 20 includes implantable medical device ("IMD") 24 within patient P, monitor 26, private network 27, patient management network 28, and patient management web clients 30 including patient browser 30a that is capable of displaying patient website 31a and clinician browser 30b that is capable of displaying clinician website 31b.

IMD 24 is, for example, a device such as a pacemaker or defibrillator that is implanted within patient P and is capable of providing life-saving and life-enhancing cardiac therapies. These therapies may include providing pacing pulses or defibrillation shocks to the heart of patient P. IMD 24 also records useful data such as, for example, without limitation, data related to the condition of patient P, therapy delivery, device performance and functionality and periodically provides that data to clinician C. IMD 24 also provides self-monitoring of the system operation (such as lead impedance data, high-voltage capacitor charge times, battery capacity, etc.). In addition, IMD 24 is capable of detecting the occurrence of an event that satisfies predefined alert criteria. The alert criteria pertain to either a clinically-relevant event or a potential abnormal functioning of the implanted device that is necessary or compelling to raise the patient's and/or clinician's attention. Once an event has been detected that satisfies an alert criterion, IMD 24 is capable of providing a patient alert and/or a silent alert. A patient alert is a patient notification of a triggered alert criteria via an audible tone vibration, or other communication directed to the patient from IMD 24 or monitor 26. A silent alert is a clinician notification of a triggered alert criteria via alert system 20.

Monitor 26 is an instrument, such as Medtronic's CareLink monitor, intended for use in a patient's home that is capable of receiving data from the patient's implanted device via telemetry and transmitting this information via phone lines or other communication platforms to private network 27 which transfers the data to patient management network 28. Private network 27 is, for example, the IP Link service from MCI which provides a private, secure, and reliable connection.

Patient management network 28 utilizes secure computer servers that collect, process and store data sent from monitor 26. This information is available to patient P and clinician C through e.g., patient management web clients 30. Patient management web clients 30 are computer systems with a browser capable of viewing web pages on the World Wide Web. At least two patient management web clients 30 are provided: a patient browser 30a and a clinician browser 30b. Patient P can access data and other information on patient website 31a via patient browser 30a. Clinician C can access data and other information on clinician website 31b via clinician browser 30b.

There are three follow-up scenarios in which clinician C can interact with IMD 24 to monitor the condition of patient P and IMD 24: standard follow-up, remote follow-up, and ambulatory follow-up. Standard follow-up is a scheduled face-to-face interaction between patient P and clinician C in order to check the patient's health and the functioning of IMD 24. Typically, the standard follow-up occurs every three to six months. Alert system 20 of the present invention reduces the number of standard follow-ups that need to take place. The remote follow-up is a scheduled electronic transmission of the data stored in IMD 24 to clinician C in order to check the health of patient P and the functioning of the patient's IMD 24. Similar to the standard follow-up, the remote follow-up typically occurs every three to six months depending upon the patient's medical condition. The remote follow-up is enabled by use of monitor 26 and patient management network 28. The ambulatory follow-up is an unscheduled and IMD-initiated electronic transmission of the data stored in IMD 24 to clinician C in order to alert clinician C to the occurrence of an event that satisfies the alert criteria and allow clinician C to check the health of patient P and the functioning of the patient's IMD 24. It has been found that standard follow-ups are time consuming, and inconvenient for both patient P and clinician C. Ambulatory follow-ups, however, can be provided by alert system 20 of the present invention to provide many benefits.

Communication between the various components of alert system 20 will now be described. Either upon the detection of an event satisfying an alert criterion, or at a scheduled time, IMD 24 is interrogated by monitor 26 over a wireless telemetry system utilizing radio frequency (RF) signals. This interrogation provides data from IMD 24 to monitor 26. Monitor 26 communicates the data to patient management network 28 over a standard telephone system from the home of patient P and through private network 27. Data is then displayed to clinician C or patient P using patient management web clients 30 utilizing the standard world-wide web ("WWW") secured communication protocol (i.e. SSL).

The alert system 20 may facilitate, without limitation, increased efficiency in which clinician C can manage patient P in the office from the patient's home; increased simplicity in how clinician C can manage patient P in the office from the patient's home; increased cost effectiveness in which clinician C can manage patient P in the office and from the patient's home; decreased need for patient P to schedule a specific time to get their device checked; decreased dependence on patient P to understand how monitoring equipment functions in order to perform a device check; reduced confusion of patient P and fear of misunderstanding or incorrectly reacting to an alert condition; reduced probability of incorrectly identifying an alert condition; increased ability of clinician C to appropriately react to an alert condition in a timely manner; increased ability of clinician C to customize alerts depending on specific patient needs; increased ability of clinician C to monitor the condition of patient P without the patient knowing, and having to increase the anxiety level of patient P unnecessarily; increased ability of clinician C to provide alternate notification methods; increased ability of clinician C to review information (EGM, trend charts, etc.) to support alert conditions; reduced doubts of patient P about the accuracy of his or her system; increased ability of clinician C to identify and react to clinical conditions and disease management issues; reduced possibility of missing an alert due to a patient not hearing an audible tone; and decreased time in which the clinician is alerted to the event.

Figure 2:
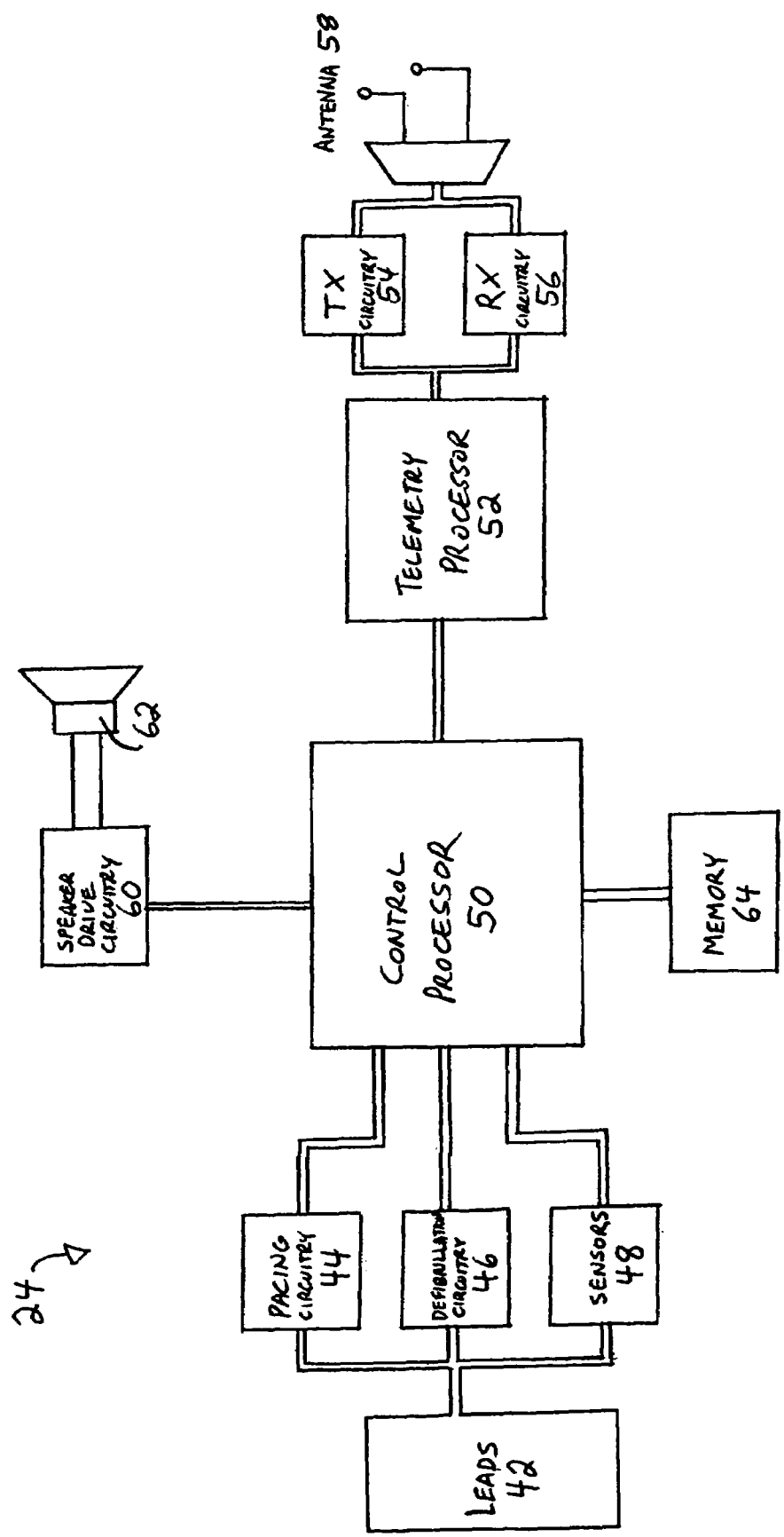
FIG. 2 is a block diagram of an IMD of the alert system of the present invention.

FIG. 2 is a block diagram of IMD 24 of alert system 20. Although it is recognized that alert system 20 can be used with any type of implantable medical device, a specific example will now be provided in which IMD 24 is an implantable cardioverter defibrillator. IMD 24 includes leads 42, pacing circuitry 44, defibrillation circuitry 46, sensors 48, control processor 50, telemetry processor 52, transmitter circuitry 54, receiver circuitry 56, antenna 58, speaker drive circuitry 60, speaker 62, and memory 64. Control processor 50 is the primary controller for IMD 24 and thus control processor 50 controls the overall operation of IMD 24.

Control processor 50 controls pacing circuitry 44 and defibrillation circuitry 46 to provide therapeutic electrical pulses to leads 42. Leads 42 are preferably implanted within the heart of patient P and provide an electrically conductive path for the pulses to selected locations within the heart. In addition, leads 42 can be used by sensors 48 to detect cardiac signals in the heart. These cardiac signals are conducted through leads 42, detected by sensors 48, and then provided to control processor 50. If desired, control processor 50 can save the signals in memory 64, which is preferably a type of random access memory (RAM) or flash memory.

Control processor 50 is capable of analyzing the cardiac signals received from sensors 48 and determining whether an event has occurred which satisfies an alert criterion. In addition, control processor 50 is capable of monitoring the condition of IMD 24 to determine whether an event has occurred which satisfies an alert criterion. If control processor 50 determines that such an event has occurred, it then decides, based upon clinician selectable alert settings, what type of an alert should be provided. If the clinician selectable alert settings instruct control processor 50 to provide a patient alert, an alert signal is generated and sent to speaker drive circuitry 60. Speaker drive circuitry 60 provides the necessary electrical signal to speaker 62 to create an audible sound which alerts patient P to the occurrence of the event.

Alternatively, if clinician selectable alert settings instruct control processor 50 to provide a silent alert, then control processor 50 instructs telemetry processor 52 to transmit a wireless telemetry signal. Telemetry processor 52 then controls transmitter circuitry 54 to create a radio frequency (RF) signal that is transmitted wirelessly over antenna 58. This signal alerts monitor 26 (FIG. 3) that IMD 24 is initiating communication, provided that monitor 26 is within the telemetry range of IMD 24. In this way, IMD 24 is capable of initiating communication with monitor 26 to inform monitor 26 of the occurrence of an event that satisfies the alert criteria. Further detail of the communication between IMD 24 and monitor 26 will be provided with reference to FIG. 3.

It is recognized that IMD 24 could be utilized to provide an alert signal in response to any detectable event as well as the absence of any detectable event. In one embodiment there are five events, the occurrence of which clinician C may choose to be notified of. The five types of events relate to therapy delivery, arrhythmias, heart failure, system integrity, and cardiac ischemia.

Therapy delivery is an event that occurs when IMD 24 delivers electrical stimulation for pain suppression pacing, defibrillation or to control another component, drug delivery, or the delivery of other materials. The alert criterion may specify, for example, that an alert should be sent for all therapies, an initial therapy, an unsuccessful therapy, a successful therapy, an attempt at providing a therapy, a delayed or aborted therapy, only after a predetermined number of therapies, a defibrillation therapy that was not able to be delivered due to an unsuccessful attempt to charge its delivery capacitor, or a defibrillation therapy that was not successfully delivered due to a short circuit present in its delivery pathway. In addition, the alert criterion may specify, for example, that an alert should be sent for a change in percentage of pacing, a change in rate responsive therapy, a change in use of therapies, or a newly detected need for a therapy.

Arrhythmic events may include, e.g., a new atrial or ventricular tachycardia, a new atrial or ventricular fibrillation, a non-sustained tachycardia, an atrioventricular nodal reentry tachycardia, a premature ventricular contraction, a detected episode with no therapy programmed, a change in duration of episodes, a frequency of episodes, a rate of arrhythmia, and a presence of rapid atrial conduction to ventricle, or when there is no intrinsic rhythm detected (asystole).

Heart failure events may include edema triggers, pressure data triggers (for example, data from a an implantable hemodynamic monitor such as the Medtronic Chronicle), heart rate variability, activity, and nocturnal heart rate changes.

System integrity events are events which indicate an abnormal functioning of IMD 24. System integrity events may include a memory failure (such as with RAM), a power-on reset (POR), a charge circuit timeout, an elective replacement indicator (ERI), device hardware failure, EEPROM failure, device initialization failure, multiple microprocessor failure, capture threshold changes, sensing threshold changes, presence of far-field R wave oversensing, myopotentials, electromechanical interference (EMI), T-wave oversensing, pacemaker modes of VOO or DOO on for more than a predetermined amount of time, device detection off or therapy off, device has not had telemetry session in a predetermined amount of time, no superior vena cava lead when active can is off, and an excessive number of non-physiologic ventricular or atrial intervals.

An ischemia event is a deficiency of blood in tissue, usually due to functional constriction or actual obstruction of a blood vessel. An example of an ischemia event is cardiac/myocardial ischemia which is a deficiency of blood supply to areas of heart tissue.

Figure 3:
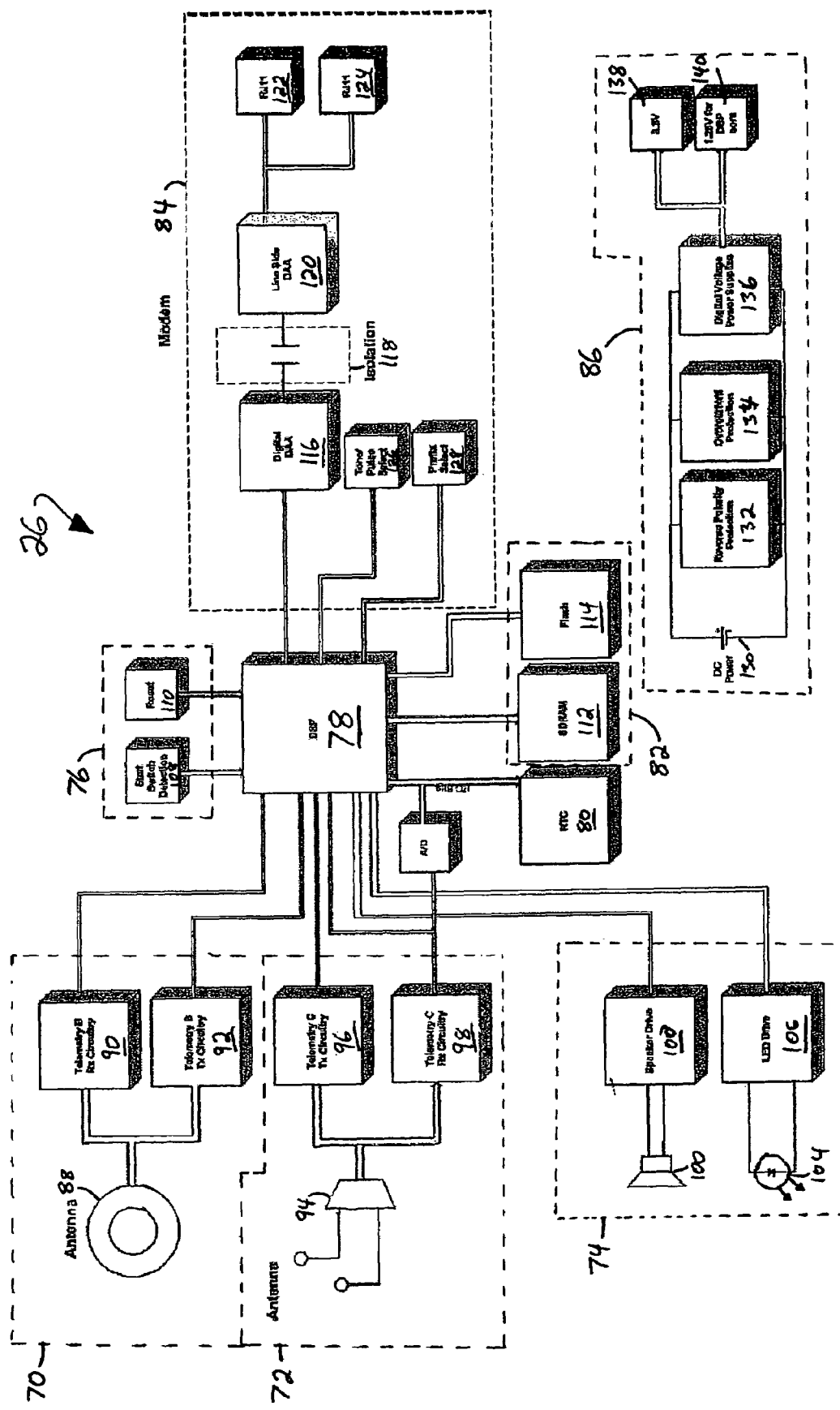
FIG. 3 is a block diagram of a monitor of the alert system of the present invention.

FIG. 3 is a block diagram of monitor 26 of alert system 20 of the present invention. Monitor 26 includes short-range (e.g., programming head) communication system 70, longer-range wireless communication system 72, patient alerts 74, control switches 76, digital signal processor ("DSP") 78, real-time clock ("RTC") 80, memory 82, modem 84, and power supply 86. Short-distance communication system 70 includes antenna 88, receiver circuitry 90, and transmitter circuitry 92. Wireless communication system 72 includes wireless antenna 94, wireless transmitter circuitry 96, and wireless receiver circuitry 98. Patient alerts include speaker 100, speaker drive 102, light-emitting diodes (LEDs) 104, and LED drive 106. Control switches 76 include start switch 108, and reset 110. Memory 82 includes SDRAM 112 and flash 114. Modem 84 includes digital data access arrangement ("digital DAA") 116, isolation 118, line side DAA 120, RJ11 ports 122 and 124, tone/pulse select 126, and prefix select 128. Power supply 86 includes DC power 130, reverse polarity protection 132, overcurrent protection 134, digital voltage power supplies 136, and DC outputs 138 and 140.

Monitor 26 is preferably located within the home of patient P. However, it is recognized that monitor 26 could be placed in other locations as well. In addition, multiple monitors could be located at different places to allow communications with IMD 24 through any one of the monitors. Monitor 26 is capable of longer-distance wireless communication with IMD 24 via wireless communication system 72. Short-distance communication system 70 is also provided to enable communication with implantable medical devices which utilize the short-distance head-based communication systems.

Antenna 88 of short-distance communication system 70 is preferably a dual opposing coil RF read head which is used to transmit data during downlinks and receive data during uplinks. Short-distance receiver circuitry 90 amplifies, filters, and digitizes the received data signal before sending it to DSP 78. Short-distance transmitter circuitry 92 receives logic level signals from DSP 78 and converts them to a higher current drive signal for RF read head antenna 88. Transmitter circuitry 92 properly tunes the antenna to the appropriate frequency for transmission. Short-distance transmitter circuitry 92 is also capable of being disabled to isolate it from antenna 88 so that it does not affect the receive circuitry during receive mode.

Wireless communication system 72 provides the capability of communicating with IMD 24 using wireless telemetry with RF signals. Wireless antenna 94 includes two separate antennas to provide spatial diversity. It is tuned to a nominal wireless telemetry carrier frequency with sufficient bandwidth to accommodate the entire medical implant communication service ("MICS") 402–405 MHz band. Wireless transmitter circuitry 96 generates the RF downlink transmission to IMD 24 in the 403–405 MHz MICS band. Wireless receiver circuitry 98 receives and demodulates the RF uplink transmission to IMD 24 in the 402–405 MHz MICS band.

Patient alerts 74 include speaker 100 coupled to speaker drive 102 and LEDs 104 coupled to LED drive 106. Speaker drive and LED drive are both controlled by DSP 78. Speaker drive 102 and speaker 100 serve two functions: to generate tones to indicate an error or alert condition, and to make modem 84 audible. Speaker drive 102 multiplexes an audible tone from DSP 78 and the modem audio. Speaker drive 102 also has the ability to take a logic level signal as an input and drive the speaker at a high enough current to meet audio sound pressure level requirements. LEDs 104 are used as visual indicators to give status indications to patient P or (clinician C) during an interrogation and modem connection. LEDs 104 also alert patient P to power status and completion of uploaded data to the server. Light from LEDs 104 is transferred to a user interface overlay via injection molded optical light pipes. LED drive 106 accepts a logic signal from DSP 78 or digital DAA 116 and drives LEDs 104 at a higher current. Switches 76 provide buttons which allow patient P to interact with monitor 26. Switches 76 include start switch detection 108 and reset 110. Start switch 108 allows patient P to instruct monitor 26 to begin an interrogation of IMD 24. Reset 110 allows patient P to reset monitor 26 to factory defined settings.

DSP 78 is responsible for the majority of the functions of monitor 26. It encodes and transmits data for both short-distance and wireless downlink transmissions, and decodes digitized data from the corresponding receiver circuitry 90 or 98 during uplink transmissions. DSP 78 is also used to implement a soft modem and directly interfaces with digital DAA 116 to send data out on a phone line. DSP 78 also runs the TCP/IP, PPP, and HTTP client software on top of the modem software. All user interface functions are handled by DSP 78 including control of patient alerts 74, as well as reading the status of tone/pulse select switch 126 and prefix select switch 128.

Real-time clock 80 is provided in monitor 26 to keep track of the time. Both IMD 24 and monitor 26 keep track of the time so that communication can take place at predetermined times. In order to save battery power in IMD 24, the telemetry system of IMD 24 does not remain active at all times. Instead, IMD 24 and monitor 26 have predefined communication times during which routine communication can take place. However, as described above, alert system 20 also includes the capability of IMD 24 initiated communication at any time in which an event is detected which satisfies the alert criteria.

Memory 82 includes SDRAM 112 and flash 114. SDRAM 112 is used to store interrogation data from IMD 24 as well as program code and other program-related data. Flash 114 is used to store program data and any parameters that need to be stored in non-volatile memory (e.g. phone numbers). DSP 78 boots from flash 114.

Modem 84 includes digital DAA 116, isolation 118, line side DAA 120, RJ-11 jacks 122 and 124, tone/pulse select switch 126, and prefix select switch 128. Digital DAA 116 along with DSP 78 and line side interface 120 form a complete V.34 modem. As described above, DSP 78 is used to implement a soft modem and directly interfaces with digital DAA 116 to send data out on a phone line. DSP 78 also runs the TCP/IP, PPP, and HTTP client software on top of the modem software. DSP 78 also reads the status of tone/pulse select switch 126 and prefix select switch 128. Tone/pulse select switch allows patient P to select whether dialing modem 84 should use tone or pulse dialing. Prefix select switch 128 allows patient P to select whether a prefix needs to be dialed to access an outside line, such as a number 9. Digital DAA 116 interfaces with DSP 78 through a serial interface and contains all of the control registers for modem 84 such as termination settings, clock phase-locked loop ("PLL") settings, etc. Digital DM 116 also includes an audio output (not shown) that is coupled to speaker drive 102 that multiplexes the modem audio and the tones generated from DSP 78. Line side DAA 120 is connected directly to the phone line via RJ-11 jacks 122 and 124. Line side DAA 120 generates DTMF signals that allow it to communicate over a telephone system to private network 27, as well as providing several other necessary functions (overload protection, programmable terminations to generate an off-hook condition for various countries, 2 to 4 wire conversion, etc.). Modem 84 isolates the line side from the other components of monitor 26 through capacitive isolation barrier 118.

Power supply 86 provides DC power to monitor 26. Power supply 86 includes DC power source 130, reverse polarity protection 132, overcurrent protection 134, digital voltage power supplies 136, and DC outputs 138 and 140. The function of power supply 86 should be easily understood by one skilled in the art and therefore will not be described in further detail.

Monitor 26 is a portable interrogation and data transfer tool used with IMD 24. Monitor 26 offers the capabilities to patient P, clinician C, and service personnel of remote interrogations, data processing, reporting and follow-up to be performed when the patient is at home and the clinician is in the clinic or a location that has web-enabled capability. This remote feature allows for reduced travel and waiting time, providing prompt care to patients and better efficiencies to clinicians. It also enables clinicians to better manage patients and still maintain the quality of care that is warranted in the marketplace. Furthermore, monitor 26 allows field representatives to increase their productivity, provide equal or better service to existing and new customers worldwide, and control costs for providing the services. The increased productivity is obtained by reducing the time required for manufacturer-assisted follow-up. Monitor 26 performs four primary functions: it interrogates IMD 24 and stores the data, it collaborates with patient management network 28 to confirm the establishment of a connection with patient management network 28, it performs any required file translation functions necessary for data transfer, and it executes the data file transfer and then collaborates with patient management network 28 to confirm that the data file transfer was successful. Although the preferred embodiment of the present invention utilizes monitor 26, it is recognized that other devices could also be used to perform the function of monitor 26. Examples of such devices include a telemetry transponder/repeater, a cell phone, or a Bluetooth-enabled or WiFi-enabled communication device.

Now that the structure of IMD 24 and monitor 26 have been described, the communications between IMD 24 and monitor 26 will be described. As explained above, clinician C and IMD 24 interact for standard follow-up, remote follow-up, and ambulatory follow-up. Of these, a remote follow-up and an ambulatory follow-up utilize monitor 26 as one of the communication links between IMD 24 and clinician C. An ambulatory follow-up occurs only when IMD 24 detects the occurrence of an event that satisfies the alert criteria and must be communicated to clinician C. A remote follow-up, on the other hand, is scheduled and expected by both IMD 24 and monitor 26, and therefore is initiated by monitor 26. This procedure also satisfies current FCC regulations for implantable medical device operating in the MICS band to initiate communications only if a "medical implant event" occurs. (Title 47 of the Code of Federal Regulations, Part 95.628.) The FCC has further defined the event as an occurrence that necessitates data exchange in order to maintain patient safety.

In any event, once communication has been established, monitor 26 performs an interrogation of IMD 24. Control processor 50 of IMD 24 reads the desired data from memory 64 and then provides it to telemetry processor 52. Telemetry processor 52 and transmitter circuitry 54 transform the data to an RF signal that is wirelessly transmitted by antenna 58 to monitor 26. Monitor 26 receives the wireless transmission of data through antenna 94 and wireless receiver circuitry 98. Receiver circuitry 98 then provides the data to DSP 78 which stores the data in SDRAM 112. After all desired data has been received, the communication between monitor 26 and IMD 24 is closed.

Figure 4:
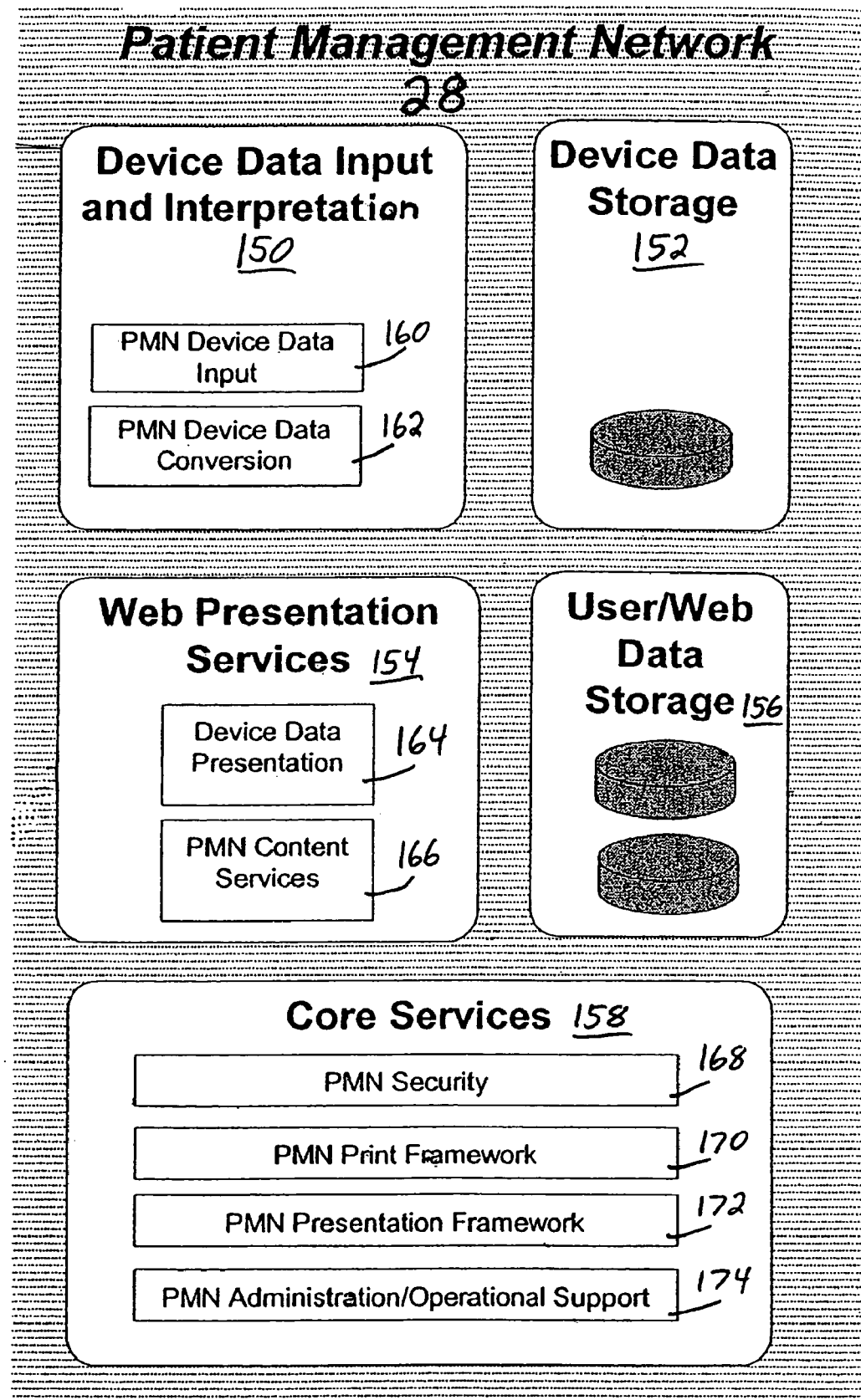
FIG. 4 is a block diagram of a patient management network of the alert system of the present invention.

FIG. 4 is a block diagram of patient management network 28 of alert system 20 of the present invention. Patient management network 28 ("PMN") includes device data input and interpretation 150, device data storage 152, web presentation services 154, user/web data storage 156, and core services 158. Device data input and interpretation 150 includes PMN device data input 160 and PMN device data conversion 162. Web presentation services 154 include device data presentation 164 and PMN content services 166. Core services 158 include PMN security 168, PMN print framework 170, PMN presentation framework 172, and PMN administration/operational support 174.

Patient management network 28 utilizes a series of secure computer servers that collect, process and store data sent from monitor 26. This data is then made available to patient P and clinician C through Internet accessible websites that are personalized for their particular needs. The patient and clinician websites will be described in further detail with reference to FIG. 5.

After monitor 26 has completed a full interrogation of IMD 24, it then transfers the data over a telephone line to private network 27. One example of private network 27 is MCI's IP Link private network. Private network 27 allows monitor 26 to remotely access patient management network 28 over a private, secure, and reliable connection utilizing the hypertext transfer protocol ("HTTP"). Patient management network, which consists of a series of secure computer servers, receives the data from monitor 26 (over the private network) and into device data input and interpretation 150, and more specifically through PMN device data input 160 which preferably includes a dedicated router. The data is then processed by PMN device data conversion 162 and stored in device data storage 152. For example, further processing is performed by web presentation services 154 to turn the raw device data into viewable portable document format ("PDF") documents, graphs, tables, etc. and also to create client and patient personalized websites which are accessed by patient browser 30a and clinician browser 30b. This data is then stored in user/web data storage 156. Additionally, core services 158 are performed by patient management system 28 to provide PMN security 168, PMN framework 170, PMN presentation framework 172, and PMN administration/operational support 174.

Figure 5:
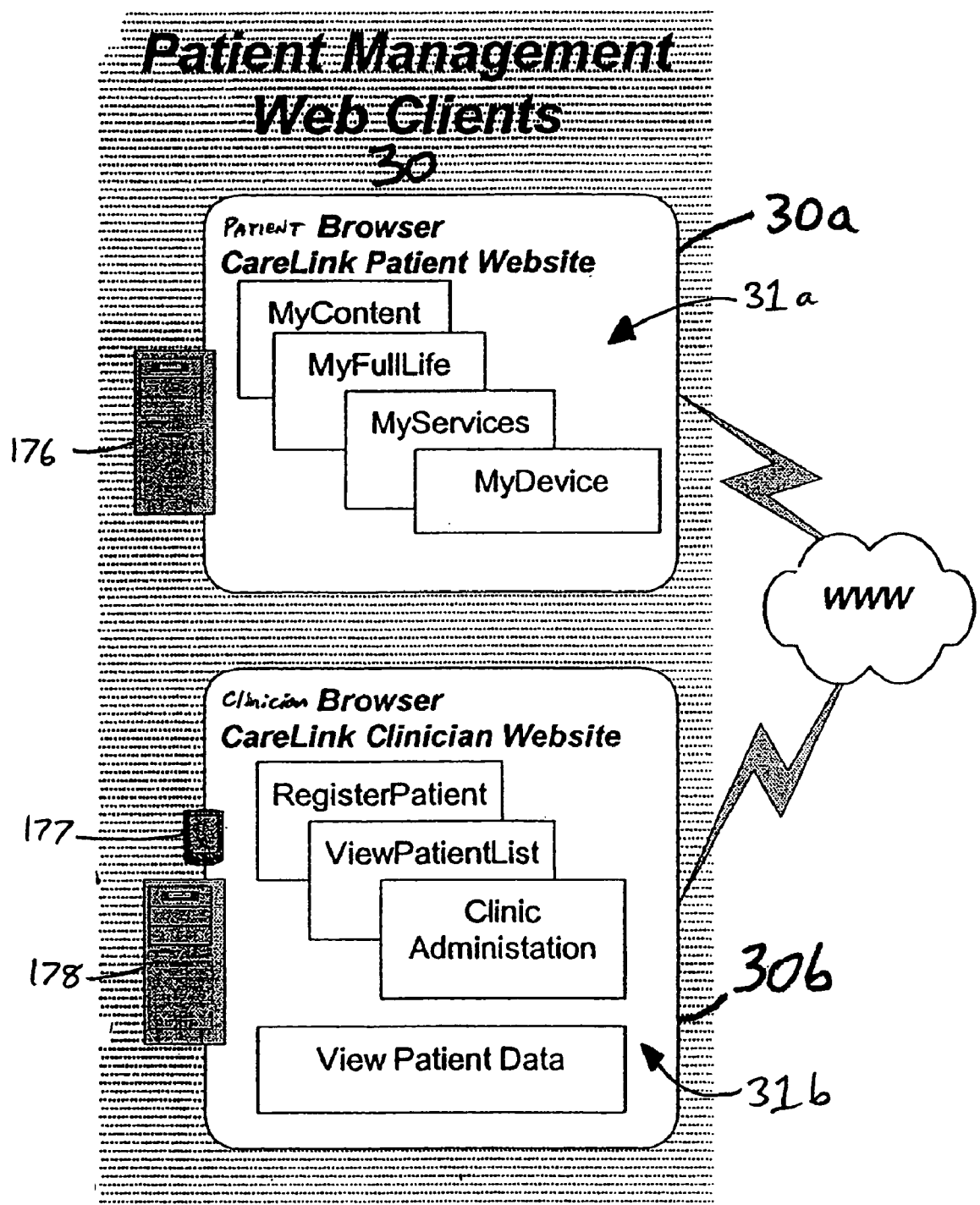
FIG. 5 is a block diagram of patient management web clients of the alert system of the present invention.

FIG. 5 is a block diagram of patient management web clients 30 of alert system 20 of the present invention. Patient management web clients 30 include patient computer 176 running patient browser 30a, and clinician's personal digital assistant ("PDA") 177 or clinician computer 178 both capable of running clinician browser 30b. Patient browser 30a is used by patient P to access the patient website 31a from patient management network 28 through the worldwide web. Clinician browser 30b is used by clinician C to access the clinician website 31b.

Patient and clinician websites 31a and 31b are both generated by patient management network 28. Patient website 31a includes: general information modules (not related to the patient's IMD data) concerning the patient's device and their disease; general ("wire feed") news items or articles containing information on medical topics of interest; psychosocial support modules designed to meet the needs of specific patient groups; access to a personalized "storefront" of products designed to meet the patient's needs; a virtual on-line community of "friends and family" that can share information and experiences with the patient; and views of IMD 24 data supplied from the device data level. Clinician website 31b includes the following capabilities: creation and maintenance of a patient list with various features for customization on a patient-specific basis; customized updates on products, clinical trials and research in addition to the provision of general ("wire-feed") news items or articles containing information on medical topics of interest; a route for clinicians to access technical services; views of stored IMD data and alerts supplied from the device data level; and means for posting information on the site that their patients can read.

Now that the structure of alert system 20 has been described, further detail will be provided as to the operation of alert system 20 of the present invention.

Figure 6:
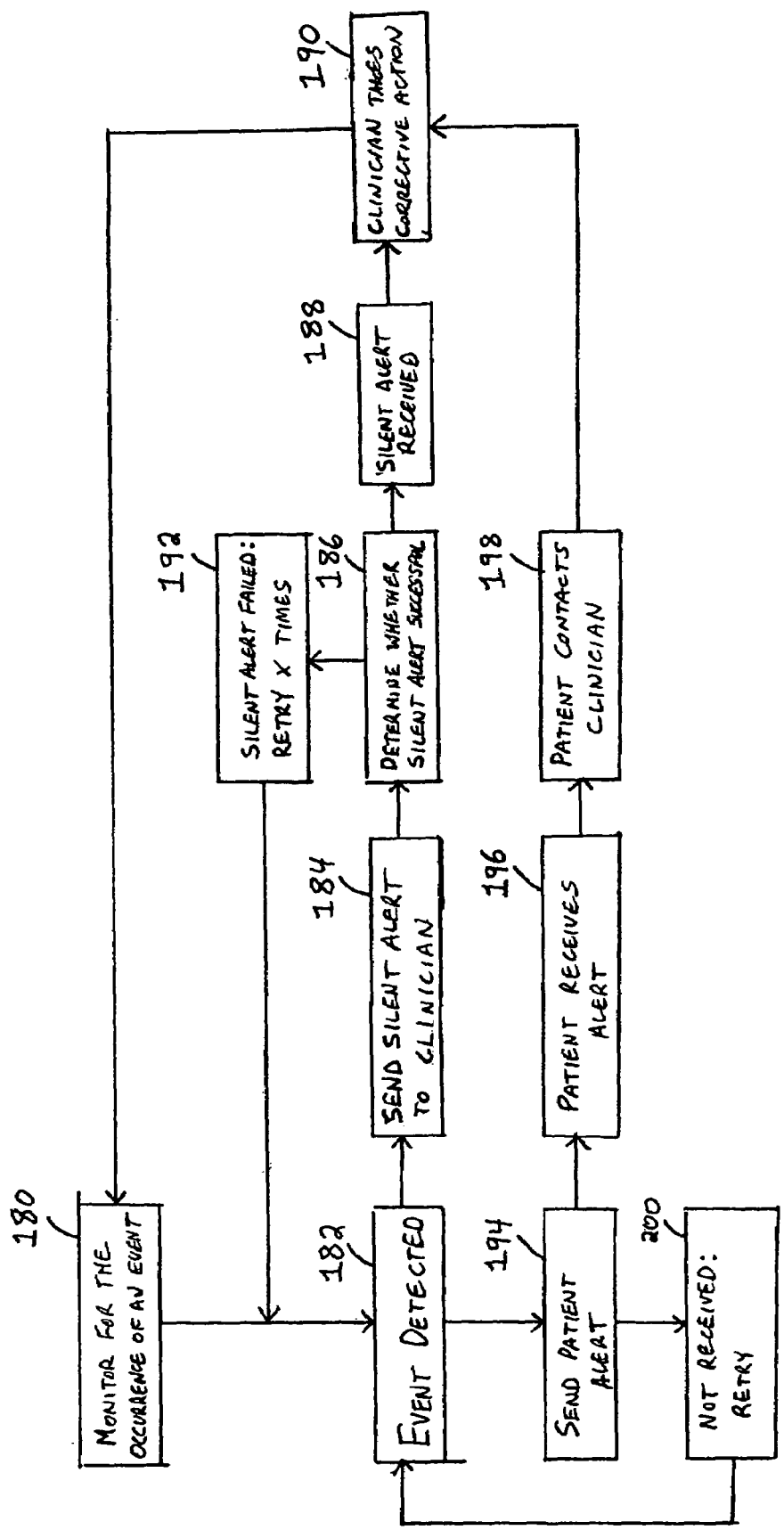
FIG. 6 is an exemplary flow diagram illustrating a method of sending an alert signal from the IMD upon the occurrence of an event satisfying alert criteria.

FIG. 6 is an exemplary flow diagram illustrating a method of sending an alert signal from IMD 24 upon the occurrence of an event satisfying the alert criteria. The method is intended only as an exemplary embodiment. IMD 24 begins by monitoring for the occurrence of an event (step 180). Once an event is detected (step 182), the system decides who should first be notified of the occurrence of the event based upon predefined alert criteria. This step is preferably performed by IMD 24, but may also be performed by monitor 26 or patient management network 28. If IMD 24 decides to attempt a silent alert to clinician C (step 184), IMD 24 wirelessly transmits an alert signal to monitor 26. If monitor 26 receives the alert signal, monitor 26 performs a full interrogation of IMD 24, as defined above, and closes the session. Monitor 26 then transfers the data to patient management network 28, which informs the clinician of the occurrence of the event. The system then determines whether the silent alert was successfully communicated to the clinician (step 186).

Various methods of determining the success of the silent alert may be used. For example, monitor 26 can provide a verification signal to IMD 24 after monitor 26 has successfully transferred the data to patient management network 28, clinician C can provide a verification signal to patient management network 28 which is then sent through alert system 20 to IMD 24, or success can be defined as a successful transfer of data from IMD 24 to monitor 26 which would require no verification signal. If alert system 20 determines that the silent alert has been received (step 188), it knows that clinician C will take the necessary corrective action (step 190). If alert system 20 determines that the silent alert has failed (step 192) (for example, if no verification signal is received in a predetermined amount of time), then IMD 24 assumes that the alert was not successfully communicated to clinician 30. As a result, IMD 24 repeats the attempted transmission a predetermined number of times (steps 182, 184, 186, and 192). Since the most frequent cause of a failed transmission is that IMD 24 is not in range of monitor 26, it is preferable to wait for a specified amount of time, such as three hours, before retrying the transmission. For example, IMD 24 will continue attempting communication every three hours for up to three days for a total of twenty four times.

If repeated attempts to transmit the alert signal are unsuccessful, IMD 24 will then switch to the backup alarm. In the exemplary embodiment, the backup alarm is the patient alert that includes speaker drive 60 and speaker 62. Thus, after repeated unsuccessful attempts to wirelessly transmit the alert signal (steps 182, 184, 186, and 192), an alert signal is sent to the patient alert (step 194). Once the patient has received the alert signal (196), patient P contacts clinician C (step 198) to inform him or her of the occurrence of an event. In an exemplary embodiment, alert system 20 will continue to provide the patient alert periodically until alert system 20 verifies that the patient alert has been received. To do so, alert system 20 detects when a full interrogation of IMD 24 has been taken place, and recognizes at that point that the patient alert has been received and that clinician C will take the appropriate corrective action (step 190).

In alternate embodiments, the patient alert may also be triggered by other situations in which the wireless transmission is considered a failure, such as: when the alert signal is not received by monitor 26, when the interrogation of IMD 24 by monitor 26 does not complete, when patient management network 28 does not receive the interrogated data, when the clinician does not acknowledge an alert after being informed by patient management network 28, or when the clinician does not log in to clinician website 31*b* via clinician browser 30*b* and check the patient's data after being alerted by patient management network 28.

Alert system 20 of the present invention provides a user interface in which clinician C can set the clinician selectable alert settings of alert system 20 to perform as desired. These settings define the alert criteria that are used by IMD 24 (or patient management network 28) to determine whether or not an alert should be sent, and whether a silent alert of a patient alert should be sent. Thus, alert system 20 provides clinician C with a user interface in which he or she can select which events should initiate a silent alert, a patient alert, both alerts, or no alert at all. Table 1 is an exemplary list of clinician selectable alert conditions. It includes the alert name, a description of the alert, and the programmable condition parameters available for that alert.

TABLE 1

Clinician Selectable Alert Conditions

| ALERT NAME | DESCRIPTION | PROGRAMMABLE CONDITION PARAMETERS |
|---|---|---|
| Lead Impedance Out of Range | A measured lead impedance trend value has exceeded the acceptable range set for the lead. | Independently enabled for each lead: If enabled, Minimum and Maximum Impedances. |
| Low Battery Voltage | The elective-replacement-indicator (ERI) battery voltage condition occurs for three consecutive days, excluding days when high voltage charges took place. | Enable/disable |
| Excessive Charge Time | Charging performance of device has met ERI indicator for charge time. | Enable/disable |
| VT/VF Therapies Exhausted | A ventricular tachyarrhythmia occurred which required delivery of all enabled therapies for the zone and failed to terminate the arrhythmia. | Enable/disable |
| Number of Ventricular CV or Defibrillation Shocks | The programmable number of shocks, or more, were delivered for a single VT/VF episode. | Enable/Disable and Number of Shocks |
| VF Therapy Disabled | The device is not in session and six hours have elapsed since the last programming and one or more of the following conditions still exist: VF detection has been disabled, or more than two VF Therapies have been disabled, or FVT is enabled to 'via VF' and more than two FVT therapies have been disabled. | Enable (High Urgency Only)/ Disable |
| High Threshold | The measured threshold for the chamber is at 5 V for 1 day. | Independently Enabled for each paced chamber |
| AT/AF Burden | The cumulative time that the patient has been in AT/AF in a given day (since midnight) has exceeded the acceptable duration as set by the clinician. | Enable/Disable: Time in AT/AF Threshold |
| Fast V Rate during AT/AF | The patient has a mean ventricular rate while in AT/AF that has exceeded the acceptable rate threshold, and AT/AF has occurred for a minimum, cumulative duration as selected by the clinician (may be a different duration than AT/AF Burden duration). Determined on a per day basis. | Enable/Disable: Ventricular Rate while in AT/AF Threshold and Min. Time in AT/AF Threshold |
| Thoracic Fluid Overload Alert | The fluid index exceeded the threshold, indicating possible thoracic fluid accumulation in the patient. | Enable/Disable, Threshold, Alert Time |

Alert system 20 not only allows clinician C to enable or disable the alert conditions, but also allows clinician C to select the response to each condition. If clinician C selects the alert mode to be "audible," the alert method is set as a patient alert. If clinician C selects the alert mode to be "silent," the alert method will be a silent alert. Finally, if the user selects the alert mode to be "audible+silent," both methods of notification will be used.

Additionally, a number of abnormalities always produce a notification and cannot be disabled by clinician C. These relate to catastrophic conditions requiring immediate follow-up and are shown in Table 2.

TABLE 2

Non-Programmable Alert Conditions

| ALERT NAME | DESCRIPTION | PROGRAMMABLE CONDITION PARAMETERS |
|---|---|---|
| Power-On Reset (POR) | A POR has occurred | No selectable parameters |
| CPU Lockout | The device has entered the CPU Lockout state | No selectable parameters |
| Charge Time-out | An attempt to charge the high voltage therapy capacitors has aborted due to a time-out | No selectable parameters |
| Incorrectly Configured Defibrillation System | The case electrode is disabled as a high voltage therapy electrode and there is no acceptable impedance for a defibrillation pathway | No selectable parameters |
| Permanent Asynchronous Mode | The programmed pacing mode was asynchronous at midnight of the device clock, and still asynchronous at the alert alarm time | No selectable parameters |

Figure 8:
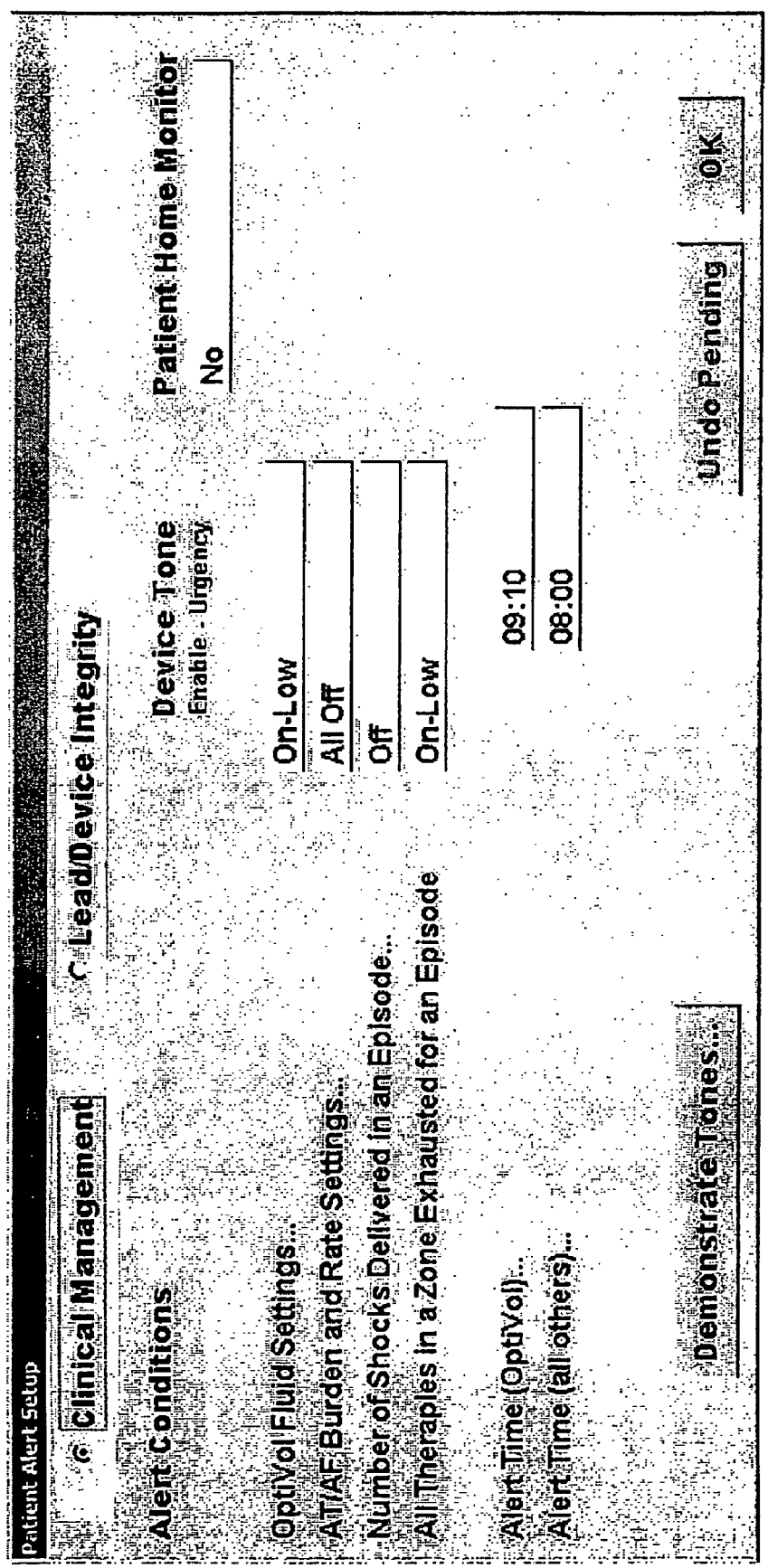
Figure 10:
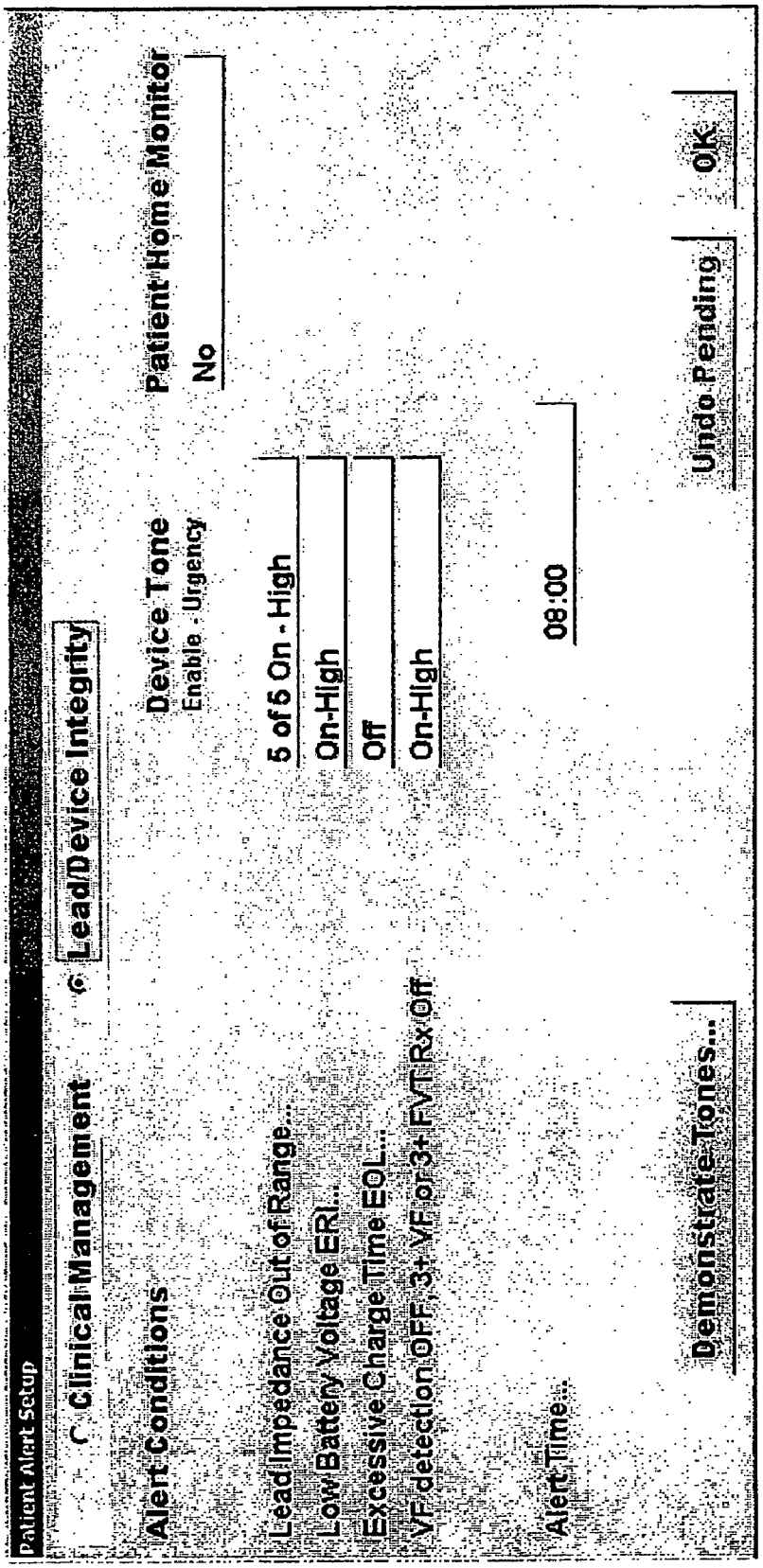

FIGS. 7–10 are exemplary screen shots of user interface 210 allowing clinician C to select clinician selectable alert settings. FIGS. 7 and 8 show clinical management alert settings and FIGS. 9 and 10 show lead/device integrity alert settings. FIG. 7 shows the dual-column clinical management alert settings that are available when "Patient Home Monitor" is set to "Yes" (enabled). FIG. 8 shows the single-column clinical management alert settings that are available when "Patient Home Monitor" is set to "No" (disabled). Similarly, FIGS. 9 and 10 show the lead/device integrity alert settings that are available when "Patient Home Monitor" is set to "Yes" or "No". User interface 210 provides a plurality of menus and sub-menus through which clinician C can select the desired alert settings. User interface 210 may be provided to clinician C in a number of different embodiments. In a first exemplary embodiment, user interface 210 is provided on a programmer for IMD 24. A programmer for an implantable medical device is well known in the art and typically includes a computer-like system having a display and input devices such as a keyboard. The programmer also includes a communication device such as an RF head or a wireless telemetry system which allows the programmer to program IMD 24. In this embodiment, user interface 210 is displayed on the display of the programmer, such that clinician C is able to select the desired alert settings. After clinician C has selected the desired settings, the programmer programs the settings into IMD 24.

In a second exemplary embodiment, user interface 210 is provided by patient management system 28. In this embodiment, user interface 210 is displayed to clinician C as a part of clinician website 31b. Clinician C is able to select the desired alert settings through clinician website 31b and then save them to patient management network 28. Patient management network 28 then initiates communication through private network 27, and monitor 26 to IMD 24 where the clinician selectable alert settings are stored in IMD 24.

To select the desired settings, clinician C first selects the type of settings that he or she wishes to set: Clinical Management Alerts (FIGS. 7 and 8) or Lead/Device Integrity Alerts (FIGS. 9 and 10). Clinical Management Alerts relate to events involving the condition of patient P, while Lead/Device Integrity Alerts relate to events involving the condition of IMD 24 and attached leads.

The user interface provides the option of enabling or disabling clinician-selectable settings for the interaction between IMD 24 and monitor 26 altogether. This feature accommodates those patients that do not have a monitor. Clinician C selects whether monitor 26 should be enabled or disabled by selecting the "Patient Home Monitor" field and selecting "Yes" or "No." If clinician C selects "Yes" then clinician-selectable silent alert options are enabled (FIGS. 7 and 9). If clinician C selects "No" then all silent alert options are disabled (FIGS. 8 and 10).

The desired settings are then selected from the menu and sub-menus as desired. For example, if clinician C wants to be alerted to an atrial tachycardia within patient P that exceeds a certain duration or exceeds a certain rate, clinician C would select the option that reads "AT/AF Burden and Rate Settings . . . ." Clinician C would then be provided with a sub-menu in which he or she could select the type of alert desired, the urgency of the alert, and the duration or heart rate at which the alert would trigger. In addition, clinician C is also able to select the specific time of the day in which a patient alert ("device tone") is provided by selecting "Alert Time . . . ." Alert settings for Lead/Device Integrity Alerts are similarly chosen through the menus as shown in FIGS. 9 and 10 and additional sub-menus.

Alert system 20 of the present invention provides many benefits and features over any known systems of the prior art. It provides multiple alerts which can be provided to various people based upon clinician-selectable alert settings, thereby increasing the safety and quality of life of a patient. It provides a system and method for transferring data automatically without any interaction by the patient. It reduces the number of times that the patient must travel to a clinic for routine checkups, thereby reducing the burden on the patient and increasing the efficiency of the clinician.

Although alert system 20 of the present invention has been described with reference to preferred embodiments, workers skilled in the art will recognize that changes may be made in form and detail without departing from the spirit and scope of the invention. The inventors have contemplated many changes which will be readily understood by one skilled in the art. For example, the alert system includes a number of patient alert methods including a speaker in IMD 24 and a speaker and LED's in monitor 26. Other known types of patient alerts may also be used including muscle stimulation, vibration, or olfactory stimulation (in an external device such as monitor 26). Furthermore, multiple patient alerts may be provided such that clinician C can select the most desired alert for the particular event. Similarly, various means of alerting the clinician (or any other person) are contemplated. An alert may be provided to a device worn or nearby a clinician such as a telemetry enabled watch, home PC, public access transponder, WiFi/Bluetooth network, telephone, pager, cell phone, or displayed on a programmer during the next interrogation. Alternatively, the alert could be provided to a call center from monitor 26 or patient management network 28, the call center having an operator who would contact the clinician. The alerts may include all information from the interrogation of IMD 24, or it may be simply a message informing clinician C to check clinician website 31b. Furthermore, a silent alert may be provided to alert patient P of the occurrence of an event in the same way that a silent alert is provided to alert clinician C of the occurrence of an event.

The exemplary embodiments of the invention store the clinician-selectable alert settings in memory 64 of IMD 24. It is recognized that the alert settings may also be stored in other locations such that other methods may be utilized. For example, clinician-selectable alert settings can be stored only on patient management network 28. In this embodiment, IMD 24 would send an alert signal to monitor 26 upon the occurrence of any possible event. Monitor 26 would then transfer the alert to patient management network 28. Patient management network 28 would then inform clinician C of the event only if the settings for that particular alert had been programmed ON. In another exemplary embodiment, the clinician-selectable alert settings are again stored on patient management network 28. IMD 24 then provides an alert signal frequently (preferably more than one per day) and the patient management network 28 would inform clinician C only if an event were detected which matched an event that was programmed ON in the clinician-selectable alert settings. Although these embodiments reduce the amount of memory needed on IMD 24 (or increase the amount of memory available for other data storage), they also decrease the longevity of the battery of IMD 24 by requiring more frequent transmission of data.

Furthermore, the alert system 20 is capable of providing an alert when an event is detected by IMD 24. It is recognized that this alert may be provided for any event which can be detected by IMD 24, or any other device in the system, or a system in communication with any device in the system. The event may include an event internal to IMD 24, within patient P, or external to patient P. Sensors capable of detecting the event may include any known sensor such as cardiac sensors, blood sensors, neurological sensors, a global positioning system receiver, microphones, magnetic sensors, pressure sensors, temperature sensors, impact sensors, electric or magnetic field sensors, vibration sensors, chemical sensors, light sensors, radiation sensors, etc. In addition, control processor 50 can be utilized to perform calculations, check for patterns, or otherwise process data and provide an alert based upon a predetermined criterion. Thus, it should be understood that the alert system of the present invention provides enormous possibilities for improving the safety of patients, increasing the quality of care that they receive, and increasing their quality of life.

The invention claimed is:

1. A method of alerting a clinician to the occurrence of an event within a patient, the method comprising:
    detecting the occurrence of the event with an implantable medical device, the implantable medical device being implanted within the patient;
    wirelessly transmitting an alert signal from the implantable medical device to alert the clinician to the occurrence of the event;
    determining whether the alert signal was successfully communicated; and
    alerting a patient to the occurrence of the event if it is determined that the alert signal was not successfully communicated.

2. The method of claim 1, wherein determining whether the alert signal was successfully communicated comprises determining whether the alert signal was received by a monitor.

3. The method of claim 1, wherein determining whether the alert signal was successfully communicated comprises determining whether an interrogation of the implantable medical device by a monitor was completed.

4. The method of claim 1, wherein determining whether the alert signal was successfully communicated comprises determining whether a patient management network received the alert signal.

5. The method of claim 1, wherein determining whether the alert signal was successfully communicated comprises determining whether the clinician has acknowledged receipt of the alert from a patient management network.

6. The method of claim 1, wherein determining whether the alert signal was successfully communicated comprises determining whether the clinician has received data related to the patient after being alerted by a patient management network.

7. The method of claim 1, wherein attempting to wirelessly transmit an alert signal comprises wirelessly transmitting an alert signal to a monitor, the method further comprising:
    receiving the alert signal with the monitor such that the attempt to wirelessly transmit the alert signal is successful;
    performing a wireless interrogation of the implantable medical device to wirelessly transfer data from the implantable medical device to the monitor;
    transferring the data from the monitor to a patient management network;
    storing the data on the patient management network; and
    creating a web page from the stored data to alert the clinician to the occurrence of the event.

8. The method of claim 7, further comprising creating a second web page from the stored data to provide supplemental information to the patient related to the event.

9. The method of claim 7, wherein transferring the data from the monitor to the patient management network comprises:
    transferring the data over a telephone line to a private network; and
    transferring the data over the private network to the patient management network.

10. The method of claim 1, wherein detecting the occurrence of the event comprises detecting the occurrence of an event relating to a therapy delivery.

11. The method of claim 1, wherein detecting the occurrence of the event comprises detecting the occurrence of an event relating to an arrhythmia.

12. The method of claim 1, wherein detecting the occurrence of the event comprises detecting the occurrence of an event relating to heart failure.

13. The method of claim 1, wherein detecting the occurrence of the event comprises detecting the occurrence of an event relating to system integrity.

14. The method of claim 1, wherein detecting the occurrence of the event comprises detecting the occurrence of an event relating to ischemia.

* * * * *

UNITED STATES PATENT AND TRADEMARK OFFICE
CERTIFICATE OF CORRECTION

| | |
|---|---|
| PATENT NO. | : 7,265,676 B2 |
| APPLICATION NO. | : 10/977242 |
| DATED | : September 4, 2007 |
| INVENTOR(S) | : Paul G. Krause et al. |

It is certified that error appears in the above-identified patent and that said Letters Patent is hereby corrected as shown below:

On the Title Page Item (75), first-named Inventor, delete "Paul G. Gordon" and insert in place thereof
--Paul G. Krause--

Signed and Sealed this

Tenth Day of February, 2009

JOHN DOLL
*Acting Director of the United States Patent and Trademark Office*